United States Patent
Van Venrooij et al.

(10) Patent No.: US 7,335,724 B2
(45) Date of Patent: *Feb. 26, 2008

(54) PEPTIDES IMMUNOREACTIVE WITH AUTOANTIBODIES FROM PATIENTS SUFFERING FROM RHEUMATOID ARTHRITIS

(75) Inventors: Waltherus Jacobus Wilhelmus Van Venrooij, Nijmegen (NL); Gerardus Antonius Schellekens, Den Bosch (NL); Jozef Maria Hendrik Raats, Nijmegen (NL); Rene Michael Antonius Hoet, Nijmegen (NL)

(73) Assignee: Stichting Voor de Technische Wetenschappen, Utrecht (NL)

( * ) Notice: Subject to any disclaimer, the term of this patent is extended or adjusted under 35 U.S.C. 154(b) by 0 days.

This patent is subject to a terminal disclaimer.

(21) Appl. No.: 11/059,775

(22) Filed: Feb. 16, 2005

(65) Prior Publication Data

US 2005/0186201 A1 Aug. 25, 2005

Related U.S. Application Data

(63) Continuation of application No. 09/308,150, filed as application No. PCT/NL97/00624 on Nov. 14, 1997, now Pat. No. 6,858,438.

(30) Foreign Application Priority Data

Nov. 15, 1996 (NL) ................... 1004539

(51) Int. Cl.
C07K 5/12 (2006.01)
C07K 7/50 (2006.01)
C07K 7/64 (2006.01)

(52) U.S. Cl. ............. 530/317; 530/324; 530/325; 530/326; 530/327; 530/328; 530/329; 530/330; 530/331; 530/350; 435/7.1; 435/7.95; 436/506

(58) Field of Classification Search ............ 530/317, 530/324–331, 350; 435/7.1, 7.95; 436/506
See application file for complete search history.

(56) References Cited

U.S. PATENT DOCUMENTS 5,888,833 A 3/1999 Serre
6,858,438 B2 * 2/2005 Van Venrooij et al. ..... 436/509
6,890,720 B1 5/2005 Serre et al.

FOREIGN PATENT DOCUMENTS

WO WO-95/34312 12/1995
WO WO-99/35617 7/1999

OTHER PUBLICATIONS

Harding, C.R. et al. J. Molec. Biol. [1983] 170(3):651-673.*
Abaza et al., J. Biol. Chem. (1992) 11:433-444.
Gan, Biochemistry (1990) 29:9432-9440.
Girbal-Neuhauser et al., J. of Immunology (1999) 162:585-594.
Hoet et al., Annals of the Rheumatic Diseases (1991) 50:611-614.
Misaki et al., J. Biol. Chemistry (1994) 269:4240-4246.
Schellekens et al., Arthritis and Rheumatism (1997) 40:S276.
Schellenkens et al., Arthritis and Rheumatism (2000) 43:155-163.
Schellekens et al., J. Clin. Invest. (1998) 101:273-281.
Seggag et al., Journal of Clinical Investigation (1995) 95:2672-2679.
Simon et al., J. of Clin. Invest. (1993) 92:1387-1393.
Tarsca et al., J. Biol. Chem. (1996) 271:30709-30716.
Van Jaarsveld et al., Clinical and Experimental Rheumatology (1999) 17:689-697.
Simon et al., J. Invest. Dermatol. (1995) 105:432-433.
Simon et al., Clin. Exp. Immunol. (1995) 100:90-98.

* cited by examiner

*Primary Examiner*—Christina Chan
*Assistant Examiner*—F. Pierre VanderVegt
(74) *Attorney, Agent, or Firm*—Morrison & Foerster LLP

(57) ABSTRACT

The invention relates to a peptide derived from an antigen recognized by autoantibodies, which peptide is reactive with autoimmune antibodies from a patient suffering from rheumatoid arthritis. The peptide according to the invention possesses a modified arginine residue. The invention also relates to antibodies against the peptide and a method of detecting autoimmune antibodies.

12 Claims, 1 Drawing Sheet

I 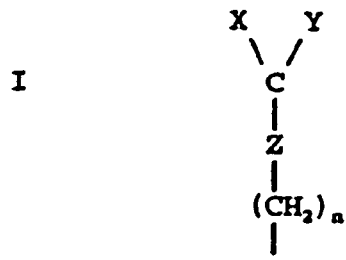
| | | |
|---|---|---|
| II | S H Q E S T X G R S R G R S G R S G S | SEQ ID NO 1 |
| III | S H Q E S T R G X S R G R S G R S G S | SEQ ID NO 2 |
| IV | S H Q E S T R G R S X G R S G R S G S | SEQ ID NO 3 |
| V | S H Q E S T R G R S R G X S G R S G S | SEQ ID NO 4 |
| VI | S H Q E S T R G R S R G R S G X S G S | SEQ ID NO 5 |
| VII | S H Q E S T X G X S R G R S G R S G S | SEQ ID NO 6 |
| VIII | S H Q E S T X G R S X G R S G R S G S | SEQ ID NO 7 |
| IX | S H Q E S T X G R S R G X S G R S G S | SEQ ID NO 8 |
| X | S H Q E S T X G R S R G R S G X S G S | SEQ ID NO 9 |
| XI | H Q C H Q E S T X G R S R G R C G R S G S | SEQ ID NO 10 |

PEPTIDES IMMUNOREACTIVE WITH AUTOANTIBODIES FROM PATIENTS SUFFERING FROM RHEUMATOID ARTHRITIS

CROSS-REFERENCE TO RELATED APPLICATIONS

This application is a continuation of U.S. Ser. No. 09/308,150 filed 30 Sep. 1999, now U.S. Pat. No. 6,858,438, which is the national phase of PCT application PCT/NL97/00624 having an international filing date of 14 Nov. 1997, which claims priority from Netherlands application 1004539 filed 15 Nov. 1996. The contents of these documents are incorporated herein by reference.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 595402000101seqlist.txt | May 2, 2007 | 19,474 bytes |

The present invention relates to a peptide derived from an antigen recognized by autoantibodies from patients with rheumatoid arthritis, which peptide is reactive with autoimmune antibodies from a patient suffering from rheumatoid arthritis.

Such a peptide is known from the European patent application 0 511 116 (Clonatec S. A.). This application describes an antigen comprising a filaggrin or profilaggrin fragment. The peptide is recognized by rheumatoid arthritis-specific autoimmune antibodies. Rheumatoid arthritis (RA) is a systemic autoimmune disease. It is the most commonly occurring inflammatory disease of the joints, it is chronic and may lead to severe physical disablement.

The object of the present is to provide a peptide which is reactive with autoimmune antibodies from a patient suffering from rheumatoid arthritis, which peptide is suitable for diagnostic research with increased specificity while also being useful for other purposes such as obtaining (raising, selecting and isolating) poly- and monoclonal antibodies.

To this end the peptide according to the invention is characterized in that the derived peptide that is reactive with autoimmune antibodies, corresponds to a part of a mRNA molecule coding for the antigen, said part comprising a codon for an arginine residue, and the arginine residue in the derived peptide, which is reactive with autoimmune antibodies, is a modified arginine residue.

Surprisingly, the peptide according to the invention that possesses a modified arginine residue, proved to be very suitable for the specific diagnosis of rheumatoid arthritis.

To this day, no specific serological test is available for RA. The only test frequently employed is based on the determination of rheumatoid factors (RF; Ref. 1) which are found in 70% of the RA patients. However, this test is not very specific and is characterized by a relatively large number of false positives. For patients suffering from systemic lupus erythematosus the percentage of false positives is approximately 20% and for healthy individuals approximately 5%.

Preferably the peptide is characterized in that the modified arginine residue's side chain is a side chain according to Formula I on the formula sheet, in which $X=NH_2$, $CH_3$, $NHCH_3$ or $N(CH_3)_2$;
$Y=O$, $NH$, $NHCH_3$ or $N(CH_3)_2$;
$Z=O$, $NH$ or $CH_2$; and
$n=2$, 3 or 4, on the condition that when $X=NH_2$ and $Z=NH$, Y is not NH; and the modified arginine residue is in particular a citrulline residue. For citrulline, $X=NH_2$, $Y=O$, $Z=NH$ and $n=3$.

A preferred peptide is the peptide selected from the group of peptides having the Formula II-X on the formula sheet.

By using the peptide according to Formula II, it is possible to establish the presence of rheumatoid arthritis in about 36% of patients actually suffering from rheumatoid arthritis, while the percentage of false positives for other autoimmune diseases and healthy individuals is less than 2%.

According to a favourable embodiment the peptide is a cyclic peptide, for instance, due to the presence of a cystine residue.

In some cases such a cyclic peptide exhibits an increased immunological affinity.

The preferred cyclic peptide is the peptide having the Formula XI on the formula sheet.

Preferably the peptide is a synthetic peptide.

The reactive peptide according to the invention can be obtained pure and in large quantities by means of organic synthesis, making immunological testing on a large scale possible.

According to an alternative embodiment, the peptide in accordance with the invention is characterized in that the peptide is obtained by the proteolytic treatment of (pro) filaggrin, separation of peptide fragments formed by proteolysis and subsequent selection on the presence of a modified arginine residue in a peptide which was formed during the proteolytic treatment.

In this manner peptides can be identified which can increase the sensitivity of a rheumatoid arthritis test. The term sensitivity is in the present application to be understood to mean the ability of a test to properly identify a patient suffering from rheumatoid arthritis.

According to a favourable embodiment, the antigen is (pro) filaggrin (SEQ ID NO: 19), and the peptide is reactive with a rheumatoid arthritis patient's autoimmune antibodies which are reactive with (pro) filaggrin.

The peptide has been shown to be very suitable for high-specificity testing (few false positives) for rheumatism.

The present invention also relates to an antibody which is cross-reactive with an antibody raised against a peptide according to the invention.

Such an antibody is useful for the indication of rheumatoid arthritis by analysing sections of biopsy samples and immunological tests of the sandwich type.

The antibody is preferably a monoclonal antibody.

According to another preferred embodiment, the antibody is obtained by using as antigen a peptide in accordance with the invention.

A suitable antibody according to the invention is characterized in that it is cross-reactive with the antibody as produced by *Escherichia coli* TG1 with plasmid RA3, deposited at the Centraalbureau voor Schimmelcultures, at Baarn, the Netherlands under accession number CBS143.96.

The invention further relates to an organic compound comprising a part that is able to compete with a peptide of the invention for binding to an antibody which is specific for said peptide, wherein at least said part of the organic compound can be prepared by means of combinatorial chemistry.

Such organic compounds are found by competitive selection wherein a peptide of the invention competes for recognition by an antibody of the invention, such as the antibody produced by *E. coli* CBS143.96. The organic compounds, which are often cheaper to produce than antigens that are prepared solely on the basis of amino acids that may or may not comprise side chains, are suitable for immunological kits for diagnosing RA. Also, after coupling to a solid carrier, said organic compounds could be applied to lower, through adsorption, the level of autoimmune antibodies in the blood of patients suffering from RA.

Finally, the invention relates to a method of detecting autoimmune antibodies against rheumatoid arthritis.

The method according to the invention is characterized in that in an immunological test at least one immunologically active molecule selected from the group consisting of i) a peptide according to the invention; ii) a recombinatory organic molecule according to the invention; and iii) an antibody according to the invention is used.

In addition to increased sensitivity other advantages are achieved, in particular better reproducibility, quantitative information and better applicability for prognostic purposes.

To a person skilled in the art it will be apparent that there are a number of possible variations to the present invention as specified by the appended claims. For instance, the peptides mentioned on the formula sheet may also be part of other oligopeptides. They may be provided at one or both ends with one or more other amino acids while also, two or more peptides according to the invention may be part of one oligopeptide. It is also possible to shorten the peptides by one or more amino acids, provided this does not have a significantly adverse effect on the reactivity. The expert is familiar with the manner in which peptides and organic compounds according to the invention may optionally be labelled or be coupled to a carrier, and how on the basis of such antigens an immunological test may be developed, using the standard techniques well-known in the field.

The invention will now be explained in more detail by means of the following example.

Materials and Methods

Peptide synthesis: Peptides were selected for synthesis on the basis of amino acid sequences derived from known cDNA sequences of human profilaggrin (Ref. 2; Ref. 3). The peptides were synthesized on solid phase using the method described by Schellekens et al. (Ref. 4). The peptides were at least 95% pure, as determined by the elution profile by means of reversed phase chromatography and the relative absorption at 214 nm. The composition of the peptides was confirmed by means of mass spectrometry (MALDI-MS). All peptides were synthesized as peptide amides.

TABLE 1

Synthesized peptides
The peptide names starting with "cf" are based on the C-terminal end (amino acids 306-324); and the peptide names staring with "nf" are based on the sequence near the N-terminal end (amino acids 18-32 for nfc1). Amino acid sequences based on cDNA of a profilaggrin repeat.

| Name | Peptide sequence* | SEQ ID NO. |
|---|---|---|
| cfc1 | S H Q E S T X G R S R G R S G R S G S | 1 |
| cfc2 | S H Q E S T R G X S R G R S G R S G S | 2 |
| cfc3 | S H Q E S T R G R S X G R S G R S G S | 3 |
| cfc4 | S H Q E S T R G R S R G X S G R S G S | 4 |
| cfc5 | S H Q E S T R G R S R G R S G X S G S | 5 |
| cfc6 | S H Q E S T X G X S R G R S G R S G S | 6 |
| cfc7 | S H Q E S T X G R S X G R S G R S G S | 7 |
| cfc8 | S H Q E S T X G R S R G X S G R S G S | 8 |
| cfc9 | S H Q E S T X G R S R G R S G X S G S | 9 |
| cf | S H Q E S T R G R S R G R S G R S G S | 11 |
| cfA | S H Q E S T A G R S R G R S G R S G S | 12 |
| cfE | S H Q E S T E G R S R G R S G R S G S | 13 |
| cfQ | S H Q E S T Q G R S R G R S G R S G S | 14 |
| nfc1 | T G P S T R G R Q G S X H E | 15 |
| nf | E S S H G W T G P S T R G R Q G S R H E | 16 |

*(A = alanine; G = glycine; H = histidine; E = glutamic acid; P = proline; R = arginine; Q = glutamine; S = serine; T = threonine; W = tryptophan; X = citrulline)

Detection by Means of ELISA

Via an N-oxysuccinimide surface the peptides were covalently coupled to the wells of 96-well microtitre plates (Costar amide binding plates) in an amount of 1 µg/well. Coupling took place for 16 hours at 4EC and pH 9.0. The plates were blocked for 1 hour with 2% bovine serum albumin. The sera were diluted 200 times in a diluent (0.3% BSA, 350 mM NaCl, 10 mM Tris-HCl pH 7.6, 1% vol./vol. Triton X-100, 0.5% w./vol. Na-deoxycholate, 0.1% SDS) supplemented with 10% normal rabbit serum, and incubated for one hour at room temperature. After washing the plates (3 times with PBS containing 0.05% by vol. of Tween® 20), 100 µl of antihuman IgG conjugated with peroxidase (Dako P214), 1000 times diluted in dilution buffer, was added to the wells. After incubation for 1 hour at room temperature, the plates were washed 3 times with PBS/Tween®, and bound antibodies were detected with tetramethyl benzidine as a substrate. After 10 minutes the reaction was stopped by adding 100 µl of 2 M sulphuric acid per well. Readout occurred at 450 nm. Sera having an $OD_{450}$ of 0.2, after deduction of the blank for the respective serum (a well without a coupled peptide), were considered to be positive.

Results

The results are listed in Table 2. In total, 288 sera from patients suffering from rheumatoid diseases were used, 132 of which were from patients suffering from rheumatoid arthritis.

TABLE 2

Results with peptide cfc1 to cfc9 (Formula II to X of the formula sheet)

| Peptide* | RA sera (%) (n = 134) | control sera[1] (%) (n = 154) | SLE[2] (%) (n = 50) | SSC[3] (%) (n = 50) | pSS[4] (%) (n = 50) | PM/DM[5] (%) (n = 50) |
|---|---|---|---|---|---|---|
| cfc1 | 49 (36) | 1 (0.6) | 1 (2) | 0 | 0 | 0 |
| cfc2 | 27 (20) | 4 (2.6) | 1 (2) | 0 | 1 (2) | 1 (2) |
| cfc3 | 37 (28) | 2 (0.6) | 0 | 0 | 1 (2) | 1 (2) |
| cfc4 | 32 (24) | 2 (1.3) | 0 | 0 | 0 | 0 |
| cfc5 | 64 (48) | 1 (0.6) | 0 | 1 (2) | 2 (4) | 1 (2) |
| cfc6 | 65 (48) | 1 (0.6) | 0 | 0 | 2 (4) | 1 (2) |
| cfc7 | 60 (45) | 1 (0.6) | 0 | 0 | 1 (2) | 1 (2) |
| cfc8 | 55 (41) | 1 (0.6) | 0 | 0 | 1 (2) | 1 (2) |
| cfc9 | 57 (42) | 1 (0.6) | 0 | 0 | 2 (4) | 0 |

[1]Control sera are from patients suffering from rheumatic diseases other than RA.
[2]SLE is systemic lupus erythematosus.
[3]pSS is primary Sjögren's syndrome.
[4]SSC is systemic scleroderma.
[5]PM/DM is polymyositis/dermatomyositis.

Of the total of 134 RA sera from patients suffering from rheumatoid arthritis, 102 were positive with at least one peptide from the cfc1 to cfc9 series. Therefore, when using these peptides, the sensitivity was 76% (102/134). Of the total of 354 control sera, 13 sera were positive on at least one peptide from the cfc1 to cfc9 series. Therefore the test sensitivity, expressed as percentage of true positives, was 96%. Of the 37 sera that were reactive with cfc3, none were not recognized by peptide cfc1 or cfc23. Of the sera that were reactive with cfc7, cfc8 and cfc9, none were not recognized by cfc1, cfc2, cfc4, cfc5 or cfc6. This means that cfc2, cfc7, cfc8 and cfc9 do not contribute to the test sensitivity and a test sensitivity of 76% may be realized by using the combination of the peptides cfc1, cfc2, cfc4, cfc5 and cfc6.

It should be noted that these percentages depend on the specificity-threshold value applied by applicants. The same data (from the ELISA experiments) can be interpreted as a sensitivity of approximately 80-85% by choosing a slightly lower sensitivity, which incidentally, is still much better than the one obtainable when using the known rheumatoid factor test (Ref. 1).

Sera from patients suffering from various infectious diseases (*Borrelia*, syphilis, malaria, endocarditis, Legionella, tuberculosis, mycoplasma, *Yersinia, salmonella*, parvovirus B19, Epstein-Barr virus, rubella, schistosomiasis, Toxoplasma, leishmaniasis, Chagas' disease) were tested for the presence of antibodies reactive with cfc1. Of the 308 tested sera 9 were positive. This means that the specificity was 97%, a considerable improvement compared with the RF test.

Variants of cfc1 wherein citrulline was replaced by a neutral (alanine; cfA), acid (glutamic acid; cfE) or amide (glutamine; cfQ) residue, did not seem to be immunologically reactive. The same applies to the control peptide cf, which does not possess a modified arginine residue.

With the aid of the above-described ELISA, a cyclic variant (with the Formula XI on the formula sheet, in which two cysteine residues (C) are bound by means of a sulphur bridge) of cfc1 was tested for 134 RA sera. This cyclic variant was shown to be reactive with 85 sera (63%), signifying an increase in sensitivity. Of the 154 sera of patients suffering from rheumatic diseases other than RA, 3 were shown to be positive (specificity 98%). The priority document of the present application reports 5 falsely determined positives. However, it has been shown that in two of these cases the patients did indeed suffer from RA. Not one serum from 59 healthy individuals was positive with this cyclic peptide, nor with any of the peptides cfc1 to cfc9. The cyclic peptide variant was shown to be reactive with 4 sera of the 200 additional control sera (50 SLE, 50 SCC, 50 pSS, 50 PM/DM) so that the specificity in respect of these sera was 98%. Of the sera from patients suffering from various infectious diseases (308 sera as described above), 7 sera were shown to be positive with the cyclic peptide variant so that in this case also the specificity in respect of these sera was 98%. The use of the cyclic peptide variant thus enhances the sensitivity compared with the individual linear peptide variants, but the specificity is also enhanced due to an improved signal/noise ratio in the described ELISA test.

A second citrulline-substituted peptide (nfc1) was shown to be specifically reactive with 10% of the RA sera, but not with the control peptide nf, which does not comprise citrulline. Of the RA sera reactive with nfc1, some were not reactive with cfc1 to cfc9. Therefore, it is possible to increase the sensitivity of a test for rheumatoid arthritis by applying more peptides comprising a modified arginine residue.

Obviously, a peptide may comprise several modified arginine residues, but the peptide may also comprise one or more non-modified arginine residues.

Applicants believe that modified amino acids, in particular those derived from arginine residues, could possibly also play a role in other autoimmune diseases. For this reason, the invention is also aimed at peptides comprising modified amino acids that are reactive with auto-antibodies from patients suffering from autoimmune diseases other than RA. This relates especially to peptides comprising a modified arginine residue wherein X=NHCH$_3$ (wherein Y=NH or NCH$_3$) or NH(CH$_3$)$_2$ is, which peptides will be useful for the detection of autoimmune diseases such as SLE, scleroderma, primary Sjögren's syndrome and polymyositis/dermatomyositis, in which nuclear autoantigens play a role. Said peptides are useful for the development of monoclonal antibodies against these diseases as well as for diagnosing the respective autoimmune diseases, in particular for the detection of autoimmune antibodies in body fluid such as blood, plasma and serum of patients who are suspected of suffering from the autoimmune disease. Again the peptides and antibodies offer the possibility of developing an organic compound with the aid of combinatorial chemistry, which compound is comprised within the scope of the invention.

The recombinant monoclonal antibody described by applicants is reactive with peptide cfc1 but not with the control peptides cfA, cfE, cfQ or cf. The commercially available monoclonal antibody AKH1 (Ref. 5), directed against human filaggrin, is not reactive with any of the peptides described herein and is therefore not cross-reactive with an antibody raised against a peptide according to the invention. The polyclonal serum anti-54 kD (Ref. 5), raised against filaggrin, is not reactive with any of the peptides described herein and is therefore not cross-reactive with an antibody reactive with a peptide according to the invention. This suggests that in a normal immune reaction antibodies that are cross-reactive with an antibody raised against a peptide according to the invention, are not necessarily formed.

REFERENCES

1) Smolen, J. S., (1996) Autoantibodies in rheumatoid arthritis, in Manual of biological markers of disease (W. J. van Venrooij and R. N. Maini, red.) vol. C Chapter 1.1 pp. 1-18. Kluwer Scientific Publishers, Dordrecht.
2) McKinley-Grant, L. J., Idler, W. W., Bernstein, I. A., Parry, D. A. D., Cannizzaro, L., Croce, C. M., Huebner, K., Lessin, S. R. & Steinert, P. M. (1989) Characterization of a cDNA clone encoding human filaggrin and localization of the gene to chromosome region 1q21. Proceedings of the National Academy of Science U.S.A. 86, pp. 4848-4852.
3) Gan, S. Q., McBride, O. W., Idler, W. W., Nedialka, M. & Steinert, P. M. (1990) Organization, structure, and polymorphisms of the human profilaggrin gene. Biochemistry 29, pp. 9432-9440.
4) Schellekens, G. A., Lasonder, E., Feijlbrief, M., Koedijk, D. G. A. M., Drijfhout, J. W., Scheffer, A. J., Welling-Wester, S & Welling, G. W. (1994) Identification of the core residues of the epitope of a monoclonal antibody raised against glycoprotein D of herpes simplex virus 1 by screening of a random peptide library. The European Journal of Immunology 24, pp. 3188-3193.
5) Hoet, R. M. A., Boerbooms, A. A. Th., Arends, M., Ruiter, D. J., van Venrooij, W. J. (1991) Antiperinuclear factor, a marker autoantibody for rheumatoid arthritis: colocalisation of the perinuclear factor and profilaggrin. Annals of the Rheumatic diseases 50, pp. 611-618.

---

The invention claimed is:

1. An antigen consisting of a cyclic peptide which peptide is a fragment of the amino acid sequence of filaggrin (SEQ ID NO: 19) and which fragment comprises an amino acid sequence derived from said filaggrin by replacing at least one arginine residue in the filaggrin amino acid sequence, with a citrulline residue,
   which antigen is specifically immunoreactive with anti-filaggrin antibodies present in the serum of subjects suffering from rheumatoid arthritis.

2. The antigen of claim 1 wherein one arginine is replaced by citrulline.

3. The antigen of claim 1 wherein two or more arginines are replaced by citrulline.

4. The antigen of claim 1 which contains at least two cysteines.

5. A method to detect rheumatoid arthritis by detecting an autoimmune antibody in the serum of a subject,
   said method comprising contacting at least two different antigens of claim 1 with said serum and detecting the presence or absence of a complex between at least one antigen and an antibody, wherein the presence of said complex detects rheumatoid arthritis.

6. The antigen of claim 1 which comprises an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10.

7. The antigen of claim 1 which is synthetic.

8. A method to detect rheumatoid arthritis by detecting an autoimmune antibody in the serum of a subject, said method comprising:
   contacting the antigen of claim 1 with said serums, and
   detecting the presence or absence of a complex between the antigen and an antibody;
   wherein the presence of said complex detects rheumatoid arthritis.

9. The method of claim 8 wherein the detecting comprises use of an antihuman antibody.

10. The method of claim 8 wherein the detecting comprises use of an enzyme-linked immunosorbent assay (ELISA).

11. The method of claim 8 wherein the antigen contains at least two cysteines.

12. The method of claim 8 wherein the antigen comprises an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10.

* * * * *

SEQUENCE LISTING

```
<160> NUMBER OF SEQ ID NOS: 18

<210> SEQ ID NO 1
<211> LENGTH: 19
<212> TYPE: PRT
<213> ORGANISM: Artificial Sequence
<220> FEATURE:
<223> OTHER INFORMATION: Derived from known cDNA sequences of human
      profilaggrin
<220> FEATURE:
<223> OTHER INFORMATION: Xaa = Citrulline

<400> SEQUENCE: 1

Ser His Gln Glu Ser Thr Xaa Gly Arg Ser Arg Gly Arg Ser Gly Arg
 1               5                  10                  15

Ser Gly Ser

<210> SEQ ID NO 2
<211> LENGTH: 19
<212> TYPE: PRT
<213> ORGANISM: Artificial Sequence
<220> FEATURE:
<223> OTHER INFORMATION: Derived from known cDNA sequences of human
     profilaggrin
<220> FEATURE:
<223> OTHER INFORMATION: Xaa = Citrulline

<400> SEQUENCE: 2

Ser His Gln Glu Ser Thr Arg Gly Xaa Ser Arg Gly Arg Ser Gly Arg
 1               5                  10                  15

Ser Gly Ser

<210> SEQ ID NO 3
<211> LENGTH: 19
<212> TYPE: PRT
<213> ORGANISM: Artificial Sequence
<220> FEATURE:
<223> OTHER INFORMATION: Derived from known cDNA sequences of human
     profilaggrin
<220> FEATURE:
<223> OTHER INFORMATION: Xaa = Citrulline

<400> SEQUENCE: 3

Ser His Gln Glu Ser Thr Arg Gly Arg Ser Xaa Gly Arg Ser Gly Arg
 1               5                  10                  15

Ser Gly Ser
```

```
<210> SEQ ID NO 4
<211> LENGTH: 19
<212> TYPE: PRT
<213> ORGANISM: Artificial Sequence
<220> FEATURE:
<223> OTHER INFORMATION: Derived from known cDNA sequences of human
      profilaggrin
<220> FEATURE:
<223> OTHER INFORMATION: Xaa = Citrulline

<400> SEQUENCE: 4

Ser His Gln Glu Ser Thr Arg Gly Arg Ser Arg Gly Xaa Ser Gly Arg
1               5                   10                  15

Ser Gly Ser

<210> SEQ ID NO 5
<211> LENGTH: 19
<212> TYPE: PRT
<213> ORGANISM: Artificial Sequence
<220> FEATURE:
<223> OTHER INFORMATION: Derived from known cDNA sequences of human
      profilaggrin
<220> FEATURE:
<223> OTHER INFORMATION: Xaa = Citrulline

<400> SEQUENCE: 5

Ser His Gln Glu Ser Thr Arg Gly Arg Ser Arg Gly Arg Ser Gly Xaa
1               5                   10                  15

Ser Gly Ser

<210> SEQ ID NO 6
<211> LENGTH: 19
<212> TYPE: PRT
<213> ORGANISM: Artificial Sequence
<220> FEATURE:
<223> OTHER INFORMATION: Derived from known cDNA sequences of human
      profilaggrin
<220> FEATURE:
<223> OTHER INFORMATION: Xaa = Citrulline

<400> SEQUENCE: 6

Ser His Gln Glu Ser Thr Xaa Gly Xaa Ser Arg Gly Arg Ser Gly Arg
1               5                   10                  15

Ser Gly Ser

<210> SEQ ID NO 7
<211> LENGTH: 19
<212> TYPE: PRT
<213> ORGANISM: Artificial Sequence
<220> FEATURE:
<223> OTHER INFORMATION: Derived from known cDNA sequences of human
      profilaggrin
<220> FEATURE:
<223> OTHER INFORMATION: Xaa = Citrulline

<400> SEQUENCE: 7

Ser His Gln Glu Ser Thr Xaa Gly Arg Ser Xaa Gly Arg Ser Gly Arg
1               5                   10                  15

Ser Gly Ser

<210> SEQ ID NO 8
<211> LENGTH: 19
<212> TYPE: PRT
<213> ORGANISM: Artificial Sequence
<220> FEATURE:
```

-continued

<223> OTHER INFORMATION: Derived from known cDNA sequences of human
      profilaggrin
<220> FEATURE:
<223> OTHER INFORMATION: Xaa = Citrulline

<400> SEQUENCE: 8

Ser His Gln Glu Ser Thr Xaa Gly Arg Ser Arg Gly Xaa Ser Gly Arg
1               5                   10                  15

Ser Gly Ser

<210> SEQ ID NO 9
<211> LENGTH: 19
<212> TYPE: PRT
<213> ORGANISM: Artificial Sequence
<220> FEATURE:
<223> OTHER INFORMATION: Derived from known cDNA sequences of human
      profilaggrin
<220> FEATURE:
<223> OTHER INFORMATION: Xaa = Citrulline

<400> SEQUENCE: 9

Ser His Gln Glu Ser Thr Xaa Gly Arg Ser Arg Gly Arg Ser Gly Xaa
1               5                   10                  15

Ser Gly Ser

<210> SEQ ID NO 10
<211> LENGTH: 21
<212> TYPE: PRT
<213> ORGANISM: Artificial Sequence
<220> FEATURE:
<223> OTHER INFORMATION: Derived from known cDNA sequences of human
      profilaggrin
<220> FEATURE:
<223> OTHER INFORMATION: Xaa = Citrulline
<220> FEATURE:
<221> NAME/KEY: Disulfide
<223> OTHER INFORMATION: (3)..(16)

<400> SEQUENCE: 10

His Gln Cys His Gln Glu Ser Thr Xaa Gly Arg Ser Arg Gly Arg Cys
1               5                   10                  15

Gly Arg Ser Gly Ser
            20

<210> SEQ ID NO 11
<211> LENGTH: 19
<212> TYPE: PRT
<213> ORGANISM: Artificial Sequence
<220> FEATURE:
<223> OTHER INFORMATION: Derived from known cDNA sequences of human
      profilaggrin

<400> SEQUENCE: 11

Ser His Gln Glu Ser Thr Arg Gly Arg Ser Arg Gly Arg Ser Gly Arg
1               5                   10                  15

Ser Gly Ser

<210> SEQ ID NO 12
<211> LENGTH: 19
<212> TYPE: PRT
<213> ORGANISM: Artificial Sequence
<220> FEATURE:
<223> OTHER INFORMATION: Derived from known cDNA sequences of human
      profilaggrin

<400> SEQUENCE: 12

```
Ser His Gln Glu Ser Thr Ala Gly Arg Ser Arg Gly Arg Ser Gly Arg
1               5                   10                  15

Ser Gly Ser

<210> SEQ ID NO 13
<211> LENGTH: 19
<212> TYPE: PRT
<213> ORGANISM: Artificial Sequence
<220> FEATURE:
<223> OTHER INFORMATION: Derived from known cDNA sequences of human
      profilaggrin

<400> SEQUENCE: 13

Ser His Gln Glu Ser Thr Glu Gly Arg Ser Arg Gly Arg Ser Gly Arg
1               5                   10                  15

Ser Gly Ser

<210> SEQ ID NO 14
<211> LENGTH: 19
<212> TYPE: PRT
<213> ORGANISM: Artificial Sequence
<220> FEATURE:
<223> OTHER INFORMATION: Derived from known cDNA sequences of human
      profilaggrin

<400> SEQUENCE: 14

Ser His Gln Glu Ser Thr Gln Gly Arg Ser Arg Gly Arg Ser Gly Arg
1               5                   10                  15

Ser Gly Ser

<210> SEQ ID NO 15
<211> LENGTH: 14
<212> TYPE: PRT
<213> ORGANISM: Artificial Sequence
<220> FEATURE:
<223> OTHER INFORMATION: Derived from known cDNA sequences of human
      profilaggrin
<220> FEATURE:
<223> OTHER INFORMATION: Xaa = Citrulline

<400> SEQUENCE: 15

Thr Gly Pro Ser Thr Arg Gly Arg Gln Gly Ser Xaa His Glu
1               5                   10

<210> SEQ ID NO 16
<211> LENGTH: 20
<212> TYPE: PRT
<213> ORGANISM: Artificial Sequence
<220> FEATURE:
<223> OTHER INFORMATION: Derived from known cDNA sequences of human
      profilaggrin

<400> SEQUENCE: 16

Glu Ser Ser His Gly Trp Thr Gly Pro Ser Thr Arg Gly Arg Gln Gly
1               5                   10                  15

Ser Arg His Glu
            20

<210> SEQ ID NO 17
<211> LENGTH: 14
<212> TYPE: PRT
<213> ORGANISM: Artificial Sequence
<220> FEATURE:
<223> OTHER INFORMATION: Derived from known cDNA sequences of human
      profilaggrin
```

```
<400> SEQUENCE: 17

Thr Gly Pro Ser Thr Arg Gly Arg Gln Gly Ser Arg His Glu
 1               5                  10

<210> SEQ ID NO 18
<211> LENGTH: 19
<212> TYPE: PRT
<213> ORGANISM: Artificial Sequence
<220> FEATURE:
<223> OTHER INFORMATION: Derived from known cDNA sequences of human
      profilaggrin

<400> SEQUENCE: 18

Ser His Gln Glu Ser Thr Gly Pro Ser Thr Arg Gly Arg Gln Gly Ser
 1               5                  10                  15

Arg His Glu
```